United States Patent
Galey et al.

(10) Patent No.: US 6,218,432 B1
(45) Date of Patent: Apr. 17, 2001

(54) DIAMINE ALKYLENE DIACETIC OR TRIACETIC ACID DERIVATIVES, PREPARATION METHOD, USE IN COSMETIC AND PHARMACEUTICAL COMPOSITIONS AND COMPOSITIONS CONTAINING THEM

(75) Inventors: Jean-Baptiste Galey, Aulnay; Jacqueline Dumats, Villepinte, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/297,748

(22) PCT Filed: Sep. 1, 1998

(86) PCT No.: PCT/FR98/01877

§ 371 Date: Jul. 14, 1999

§ 102(e) Date: Jul. 14, 1999

(87) PCT Pub. No.: WO99/12891

PCT Pub. Date: Mar. 18, 1999

(30) Foreign Application Priority Data

Sep. 9, 1997 (FR) .................................................. 97 11174

(51) Int. Cl.$^7$ ........................ A01N 37/10; A01K 31/235; C07C 229/28
(52) U.S. Cl. .............................. 514/533; 560/39; 560/41; 560/42
(58) Field of Search .............................. 514/533; 560/39, 560/41, 42

(56) References Cited

U.S. PATENT DOCUMENTS 4,528,196  7/1985  Pitt .

5,709,848  1/1998  Galey et al. .

FOREIGN PATENT DOCUMENTS

| 0 700 896 | 3/1996 | (EP) . |
| 0 755 917 | 1/1997 | (EP) . |
| WO 94/11338 | 5/1994 | (WO) . |
| WO 95/16663 | 6/1995 | (WO) . |

OTHER PUBLICATIONS

English language Derwent Abstract of EP 0 755 917.

*Primary Examiner*—Johann Richter
*Assistant Examiner*—Brian J. Davis
(74) *Attorney, Agent, or Firm*—Finnegan, Henderson, Farabow, Garrett & Dunner, L.L.P.

(57) ABSTRACT

Novel alkylenediaminediacetic acid or alkylenediaminetriacetic derivatives of formula (I):

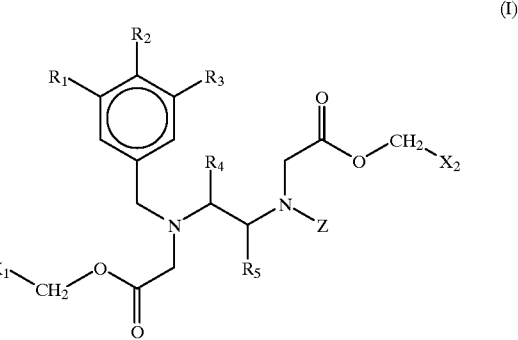

or an organic or inorganic salt thereof, their process of preparation, and their use in cosmetic and pharmaceutical compositions, such as for protecting the body against oxidative stress are discussed.

25 Claims, No Drawings

DIAMINE ALKYLENE DIACETIC OR TRIACETIC ACID DERIVATIVES, PREPARATION METHOD, USE IN COSMETIC AND PHARMACEUTICAL COMPOSITIONS AND COMPOSITIONS CONTAINING THEM

This application is a 371 of PCT FR98/01877 filed Sep. 1, 1998.

The subject-matter of the present invention is novel compounds of the type of esters derived from alkylenediaminediacetic acid or alkylenediaminetriacetic acid and in particular their use in cosmetic and pharmaceutical compositions, in particular for protecting the body against oxidative stress.

Oxidative stress characterizes a certain number of physiological and physiopathological situations during which there exists an imbalance in the antioxidant/prooxidant balance. This imbalance is reflected essentially by uncontrolled oxidative processes within living tissues which involve oxygen-comprising free radicals and which lead to the formation of oxidative damage in biological molecules and macromolecules.

A certain number of physiopathological situations induce, promote, accompany and/or are the direct consequence of oxidative stress. They are in particular inflammation, ageing, neurodegenerative diseases, exposure to UV radiation and to ionizing radiation, carcinogenesis, or the toxicity and/or mode of action of certain medicaments.

It is known that, during oxidative stress, iron is released from its normal storage sites, such as ferritin, and then becomes available to participate in certain reactions, in particular in Fenton and Haber-Weiss reactions, thus making possible the formation of hydroxyl radicals, the latter being known to be responsible for much oxidative damage.

Compounds, in particular synthetic compounds, which make it possible to protect the body against oxidative stress have been sought for a long time.

These compounds can be grouped into the following main classes:

antilipoperoxidizing agents, such as vitamin E, trolox or butylhydroxytoluene, biological reducing agents, such as reduced glutathione and its derivatives or vitamin C and its derivatives, singlet oxygen deactivators (quenchers), such as β-carotene, systems capable of decomposing hydrogen peroxide and in particular enzymes, such as catalase or peroxidases, in the presence of their co-substrates, systems for protecting against the superoxide anion, such as superoxide dismutase (SOD) or SOD-like materials, such as the Mn-desferal complex or copper diisopropyl salicylate, systems capable of decomposing organic hydroperoxides, such as glutathione peroxidase or selenium-based model systems, iron-chelating agents, such as desferal or certain hydroxypyridinones.

However, none of the known iron-chelating agents proved to be really satisfactory for the purpose of protecting the body with regard to hydroxyl radicals. Most of these protective compounds are toxic because of interference with the normal metabolism of iron, which limits their use.

Patent Application WO-94/11338 discloses novel iron-chelating agents which are effective against oxidative stress. These compounds, which are capable of forming complexes with iron, have low stability constants, which consequently decreases the toxicity risks associated with their use.

The action of these compounds is based on a novel concept, that of iron-chelating agents which can be activated in a situation of oxidative stress.

The advantage of these compounds is in particular that of limiting the potential side effects. This is because, in a normal situation, these compounds have an affinity for iron which is sufficiently weak not to displace iron from transport proteins, such as transferrin, unlike certain other powerful chelating agents, such as desferal or HBED, which have high stability constants (greater than $10^{30}$). In a situation of oxidative stress, these compounds are specifically oxidized by $H_2O_2$ to species having a strong affinity for iron which prevent its participation in the formation of HO°, resulting in the term "of activation in a situation of oxidative stress".

A number of in vitro experiments have confirmed the advantage of these compounds as protective agents with regard to the induction of oxidative damage catalysed by iron in the various classes of biological molecules.

However, the protective effect of these compounds of the prior art on cultured cells remains relatively modest because their bioavailability remains low, even when the compounds are provided in the form of alkyl esters.

The aim of the present invention is to solve this problem by providing novel compounds which are effective against oxidative stress and which confer very effective protection against the toxicity of $H_2O_2$ on cultured cells.

The subject-matter of the invention is therefore a compound of formula (I):

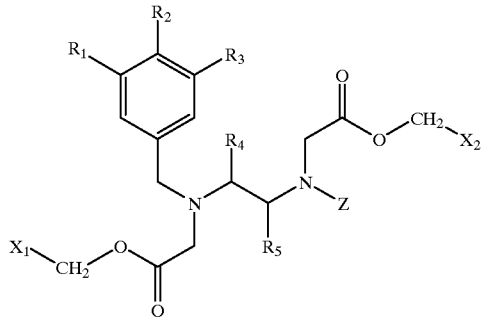

in which:

$R_1$, $R_2$ and $R_3$ are, independently of one another, chosen from H, OH or a linear or branched $C_1$–$C_8$ alkoxy radical $R_4$ and $R_5$ are, independently of one another, chosen from H or a linear or branched $C_1$–$C_4$ alkyl radical; it being possible for $R_4$ and $R_5$, taken together, to form a 5- or 6-membered ring $X_1$ and $X_2$ are, independently of one another, chosen from:

a —(CO)NR$_6$R$_7$ group in which $R_6$ and $R_7$ are, independently of one another, chosen from H or a linear or branched $C_1$–$C_4$ alkyl radical; it being possible for $R_6$ and $R_7$, taken together, to form a 5- or 6-membered ring, or an —O(CO)R$_8$ group in which $R_8$ is chosen from H or a linear or branched $C_1$–$C_8$ alkyl radical Z is chosen from a group of formula A or a group of formula B

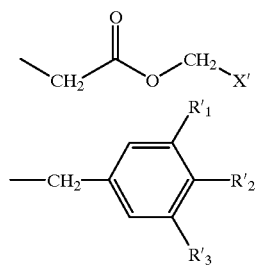

in which:

R'$_1$, R'$_2$ and R'$_3$ are, independently of one another, chosen from H, OH or a linear or branched C$_1$–C$_8$ alkoxy radical X' is either a —(CO)NR'$_4$R'$_5$ group in which R'$_4$ and R'$_5$ are, independently of one another, chosen from H or a linear or branched C$_1$–C$_4$ alkyl radical; it being possible for R'$_4$ and R'$_5$, taken together, to form a 5- or 6-membered ring; or an —O(CO)R'$_6$ group in which R'$_6$ is chosen from H or a linear or branched C$_1$–C$_8$ alkyl radical and its organic or inorganic salts.

Another subject-matter of the invention is a process for the preparation of the above compounds in which a salt, for example a sodium salt or a hydrochloride, of an N,N'-dibenzylalkylenediamine-N,N'-diacetic acid derivative or N-benzylalkylenediamine-N,N',N'-triacetic acid derivative is reacted with 2 to 4 equivalents of a substituted halomethyl derivative.

Another subject-matter of the invention is a cosmetic or pharmaceutical composition comprising, in a cosmetically or pharmaceutically acceptable vehicle, at least one compound of above formula (I).

Another subject-matter of the invention is the use of the compounds of formula (I) as antioxidizing agent.

Another subject-matter of the invention is the use of the compounds of formula (I) in a cosmetic composition for treating oxidative stress and/or for treating the effects of exposure to the sun and/or for preventing ageing, in particular of the skin or hair.

Another subject-matter of the invention is the use of the compounds of formula (I) for the preparation of a pharmaceutical composition intended to treat oxidative stress, in particular related to certain pathological conditions, and/or intended to treat pathological situations, such as cancers, inflammatory conditions, reinfusion ischaemia, iron overloads or degenerative diseases of the nervous system, and/or intended to treat the effects of exposure to ionizing or solar radiation, and/or intended to treat the effects of the use of certain medicaments which generate free radicals, and/or intended to prevent ageing, in particular of the skin or hair.

It has therefore been found that the compounds of the invention exert a protective effect at low concentrations, of the order of a few micromoles per litre, whereas the compounds of the closest prior art, such as WO 94/11338, only exert an effect at much higher concentrations, of the order of a millimole per litre.

The compounds according to the invention are therefore much more effective than those of the prior art with respect to the protection of cultured cells against the toxicity of H$_2$O$_2$.

The compounds according to the invention are therefore esters of N,N'-dibenzylalkylenediamine-N,N'-diacetic acid derivatives or N-benzylalkylenediamine-N,N',N'-triacetic acid derivatives.

They correspond to the above general formula (I).

The alkoxy radicals are preferably chosen, independently of one another, from methoxy, ethoxy, n-propyloxy, isopropyloxy, n-butyloxy, sec-butyloxy or tert-butyloxy radicals.

The alkyl radicals are preferably chosen, independently of one another, from methyl, ethyl, n-propyl, isopropyl, n-butyl, sec-butyl or tert-butyl radicals. When they form a ring, the said ring is preferably a cyclohexyl.

The compounds according to the invention can also be provided in the form of inorganic or organic acid salts.

Mention may be made, among inorganic salts, of sulphates, hydrochlorides, nitrates, phosphates or bromates.

Mention may be made, among organic salts, of fumarates, mesylates or tosylates.

Mention may in particular be made, among the preferred compounds according to the invention, of:

bis(acetoxymethyl) [N,N'-bis(3,4,5-trimethoxybenzyl)] ethylenediamine-N,N'-diacetate, bis(pivaloyloxymethyl) [N,N'-bis(3,4,5-trimethoxybenzyl)]ethylenediamine-N,N'-diacetate, and bis(N,N-diethylaminocarbonylmethyl) [N,N'-bis(3,4,5-trimethoxybenzyl)]ethylenediamine-N,N'-diacetate, and their salts, in particular their hydrochlorides.

The compounds according to the invention can be prepared by a person skilled in the art on the basis of his overall knowledge according to conventional synthetic methods.

This preparative process can consist in particular in reacting a salt, for example a sodium salt or a hydrochloride, of an N,N'-dibenzylalkylenediamine-N,N'-diacetic acid derivative or N-benzylalkylenediamine-N,N',N'-triacetic acid derivative with 2 to 4 equivalents of a substituted halomethyl derivative.

Mention may be made, among substituted halomethyl derivatives, by way of example, of bromomethyl acetate or chloromethyl pivalate.

The reaction can take place in DMF at a temperature of 35–60° C., preferably 40–50° C., for 20–30 hours, preferably 22–26 hours.

The product obtained can subsequently be purified, for example by chromatography on a silica column.

The compounds according to the invention can be used as active substances for protecting from the harmful effects of free radicals, that is to say against oxidative stress, and in particular for treating pathological situations in human or veterinary medicine, such as cancers, inflammatory conditions, reinfusion ischaemia, iron overloads or degenerative diseases of the nervous system, or for treating the effects of exposure to ionizing or solar radiation, or for treating the effects of the use of certain medicaments known to generate free radicals, in particular anticancers, such as adriamycin.

These compounds can also be used in non-pathological situations, such as exposure to the sun or ageing, in order in particular to protect the skin or hair.

The compositions, in particular cosmetic or pharmaceutical compositions, comprising one or more compounds according to the invention can be provided in various conventional forms, such as in the form of a salve, cream, ointment, gel, spray, lotion, emulsion or vesicular dispersion.

The compound of formula (I) can be present in an amount of 0.001 to 10% by weight with respect to the total weight of the composition, preferably in a proportion of 0.01 to 8% by weight, preferably of 0.1 to 5% by weight.

When the composition is a pharmaceutical composition, it can be administered in any conventional administration form, such as orally, topically or parenterally, the pharmaceutically acceptable vehicle depending on the administration form chosen.

The pharmaceutical dosage form and the amount of compound present in the composition can be easily determined by a person skilled in the art on the basis of his overall knowledge.

In the compositions according to the invention, the compound of formula (I) can be used in combination with at least one other active substance, in particular a substance for combating free radicals.

These substances can be chosen from:
antilipoperoxidizing agents, such as vitamin E, trolox or butylhydroxytoluene,
biological reducing agents, such as reduced glutathione and its derivatives or vitamin C and its derivatives,
singlet oxygen deactivators (quenchers), such as β-carotene,
systems capable of decomposing hydrogen peroxide and in particular enzymes, such as catalase or peroxidases, in the presence of their co-substrates,
systems for protecting against the superoxide anion, such as superoxide dismutase (SOD) or SOD-like materials, such as the Mn-desferal complex or copper diisopropyl salicylate,
systems capable of decomposing organic hydroperoxides, such as glutathione peroxidase or selenium-based model systems,
iron-chelating agents, such as desferal or certain hydroxypyridinones.

The compound according to the invention can also be used in combination with anti-inflammatories, UV screening agents and/or penetration promoters.

The compound of the formula (I) and the active substance can be combined within the same composition or be applied separately.

The examples below are given for the purpose of illustrating the preparation of some compounds of formula (I) and some of their uses in the pharmaceutical and cosmetic fields.

SYNTHETIC EXAMPLE 1 bis(acetoxymethyl) [N,N'-bis(3,4,5-trimethoxybenzyl)]-ethylenediamine-N,N'-diacetate of formula:

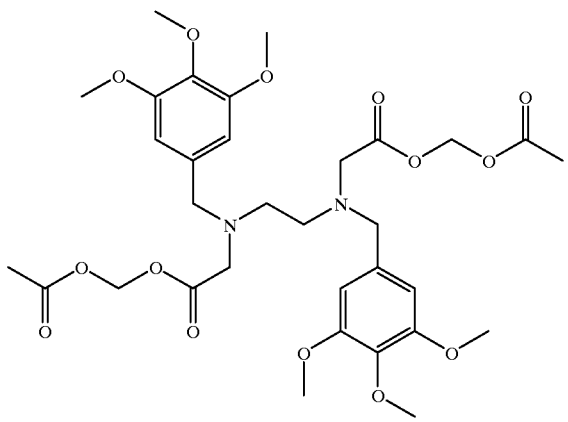

2 g (3.3 mmol) of N,N'-bis(3,4,5-trimethoxybenzyl) ethylenediamine-N,N'-diacetic acid dihydrochloride are dissolved in 20 ml of water by addition of sodium hydroxide solution. The pH is brought to 8 by addition of concentrated hydrochloric acid. The solution is evaporated to dryness and then the residue is taken up in 30 ml of dimethylformamide. 1.3 g of bromomethyl acetate ($BrCH_2OCOCH_3$; 8.5 mmol) are added and the medium is stirred at 45° C. for 24 h. The mixture is then evaporated to dryness, the residue is then taken up in dichloromethane and the solution is washed with water, dried over sodium sulphate, filtered and evaporated to dryness.

The residue is purified by chromatography on a silica column (ethyl acetate/heptane 3:1 eluent).

An oil is obtained, which oil is purified by crystallization from a dichloromethane/pentane mixture.

After filtration and drying, 650 mg of a white solid are obtained (yield: 30%).

NMR spectrum: $^1H$ and $^{13}C$ (400 MHz) in $CDCl_3$: conforms to the expected structure;
Elemental Analysis:

|  | C | H | N | O |
|---|---|---|---|---|
| % calculated | 56.46 | 6.52 | 4.12 | 32.91 |
| % found | 56.24 | 6.51 | 4.18 | 32.66 |

SYNTHETIC EXAMPLE 2 bis(pivaloyloxymethyl) [N,N'-bis(3,4,5-trimethoxybenzyl)]ethylenediamine-N,N'-diacetate of formula:

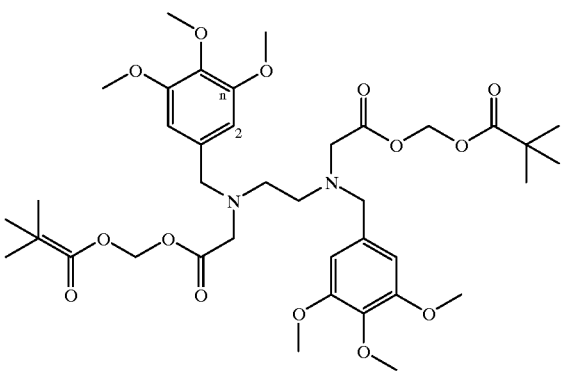

2 g (3.3 mmol) of N,N'-bis(3,4,5-trimethoxybenzyl) ethylenediamine-N,N'-diacetic acid dihydrochloride are dissolved in 20 ml of water by addition of sodium hydroxide solution. The pH is brought to 8 by addition of concentrated hydrochloric acid. The solution is evaporated to dryness and then the residue is taken up in 30 ml of dimethylformamide.

1.5 g of chloromethyl pivalate ($ClCH_2OCOtBu$; 10 mmol) are added and the medium is stirred at 45° C. for 24 h. The mixture is then evaporated to dryness, the residue is then taken up in dichloromethane and the solution is washed with water, dried over sodium sulphate, filtered and evaporated to dryness. The residue is purified by chromatography on a silica column (dichloromethane/methanol 99:1 eluent).

500 mg of a colourless oil are obtained (yield: 20%).

NMR spectrum: $^1H$ (400 MHz) in $CDCl_3$: conforms to the expected structure

SYNTHETIC EXAMPLE 3 bis(N,N-diethylaminocarbonylmethyl) [N,N'-bis(3,4,5-trimethoxybenzyl)]ethylenediamine-N,N'-diacetate dihydrochloride of formula:

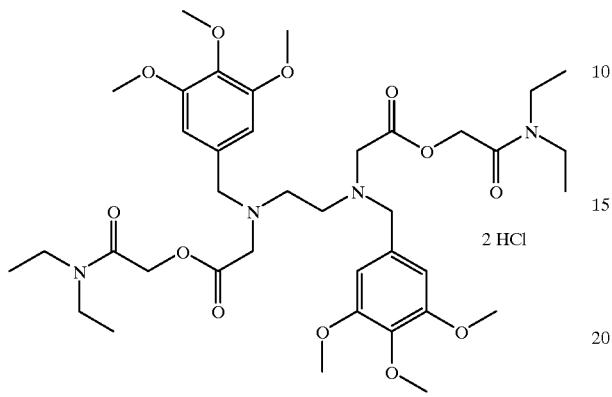

2 g (3.3 mmol) of N,N'-bis(3,4,5-trimethoxybenzyl)ethylenediamine-N,N'-diacetic acid dihydrochloride are dissolved in 20 ml of water by addition of sodium hydroxide solution. The pH is brought to 8 by addition of concentrated hydrochloric acid. The solution is evaporated to dryness and then the residue is taken up in 30 ml of dimethylformamide. 1.0 g of 2-chloro-N,N-diethylacetamide (ClCH$_2$CONEt$_2$; 6.6 mmol) and 0.1 g of methyl iodide are added and then the medium is stirred at 45° C. for 24 h. The mixture is then evaporated to dryness, the residue is then taken up in dichloromethane and the solution is washed with water, dried over sodium sulphate, filtered and evaporated to dryness. The residue is purified by chromatography on a silica column (ethyl acetate eluent).

The oil obtained is taken up in ethanol. A white precipitate appears on addition of concentrated hydrochloric acid. This precipitate is filtered off, washed with ether and dried under vacuum. 650 mg of a white solid are obtained (yield:

NMR spectrum: $^1$H (400 MHz) in CDCl$_3$: conforms to the expected structure.

EXAMPLE 4

Demonstration of the Activity of the Compounds

The activity of the compounds was evaluated by their ability to protect V79 cells against the toxicity of H$_2$O$_2$, a technique conventionally used to evaluate the effectiveness of antioxidants or iron-chelating agents.

The activity of the compound of Example 1 was compared with that of two compounds of the prior art disclosed in WO94/11338:

Comparative 1: the dihydrochloride of N,N'-bis(3,4,5-trimethoxybenzyl)ethylenediamine-N,N'-diacetic acid of formula:

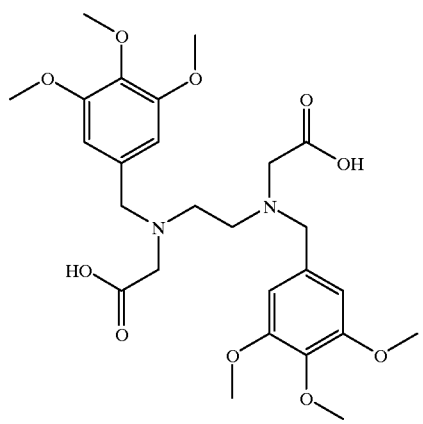

Comparative 2: its methyl ester of formula

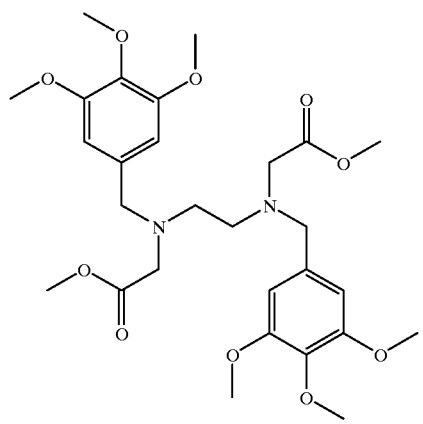

a) Experimental Protocol

V79 cells were subcultured in DMEM (Dulbecco Modified Essential Medium) medium supplemented with 10% of foetal calf serum, streptomycin, penicillin and glutamine at 37° C. under an atmosphere of 95% air +5% CO$_2$.

The cells were subsequently seeded at a density of 5×10$^3$/ml in 96-well plates.

After 24 hours, the cells were rinsed and then incubated with the test compounds at different concentrations.

After a contact time of 1 hour, 30 µM of H$_2$O$_2$ were added and incubated at 37° C. for a further one hour.

The cells were subsequently rinsed and then again brought into contact with the supplemented medium described above.

After 72 hours, the number of cells was evaluated in each well by using the neutral red technique.

The protective effect is assessed by the IC$_{50}$, which measures the concentration which induces 50% protection against cytotoxicity in comparison with the wells treated only with H$_2$O$_2$.

b) Results

The following results were obtained:

| Compound | Result (concentration inducing 50% protection) |
|---|---|
| Compound of Example 1 | 10 μM |
| Comparative 1 | 25% protection only at 10 mM |
| Comparative 2 | greater than 1 mM (compound insoluble beyond this point) |

It is therefore found that the compound according to the invention exerts a much more pronounced protective effect than those of the two compounds of the prior art.

EXAMPLE 5

A cosmetic composition which is provided in the form of an emulsion is prepared by using the constituents below (% by weight):

| | |
|---|---|
| Compound of Example 1 | 0.1% |
| Oxyethylenated PEG 50 | 3% |
| Mono/diglyceryl stearate | 3% |
| Liquid petrolatum | 24% |
| Cetyl alcohol | 5% |
| Water | q.s. for 100% |

EXAMPLE 6

A cosmetic composition which is provided in the form of an emulsion is prepared by using the constituents below (% by weight):

| | |
|---|---|
| Compound of Example 1 | 0.1% |
| Octyl palmitate | 10% |
| Glyceryl isostearate | 4% |
| Liquid petrolatum | 24% |
| Vitamin E | 1% |
| Glycerol | 3% |
| Water | q.s. for 100% |

EXAMPLE 7

The following cosmetic composition is prepared by using the constituents below (% by weight):

| | |
|---|---|
| Compound of Example 2 | 0.05% |
| Jojoba oil | 13% |
| Potassium sorbate | 0.3% |
| Cyclopentadimethylsiloxane | 10% |
| Stearyl alcohol | 1% |
| Stearic acid | 4% |
| Polyethylene glycol stearate | 3% |
| Vitamin E | 1% |
| Glycerol | 3% |
| Preservatives | q.s. |
| Water | q.s. for 100% |

EXAMPLE 8

A pharmaceutical composition in the form of a drinkable suspension is prepared comprising the following constituents:

| | |
|---|---|
| Compound of Example 1 | 0.10 g |
| 90% Ethanol | 1.00 g |
| 70% Sorbitol | 0.50 g |
| Sodium saccharinate | 0.01 g |
| Methyl p-hydroxybenzoate | 0.04 g |
| Flavouring | q.s. |
| Water | q.s. for 5 ml |

EXAMPLE 9

A pharmaceutical composition in the form of a tablet is prepared comprising the following constituents:

| | |
|---|---|
| Compound of Example 1 | 0.10 g |
| Starch | 0.12 g |
| Dicalcium phosphate | 0.20 g |
| Lactose | 0.06 g |
| Magnesium stearate | 0.02 g |

What is claimed is:

1. A compound of formula (I) or an organic or inorganic salt thereof:

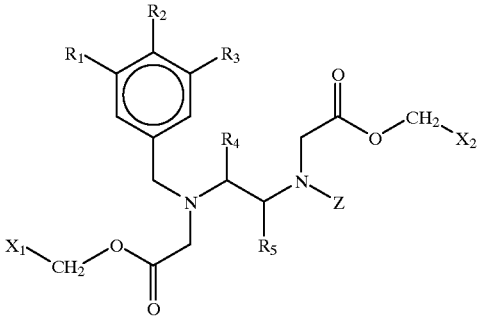

wherein:

$R_1$, $R_2$ and $R_3$ are, independently of one another, chosen from H, OH and linear and branched $C_1$–$C_8$ alkoxy radicals;

$R_4$ and $R_5$ are, independently of one another, chosen from H and linear and branched $C_1$–$C_4$ alkyl radicals; it being possible for $R_4$ and $R_5$, taken together, to form a 5- or a 6-membered ring;

$X_1$ and $X_2$ are, independently of one another, chosen from —(CO)$NR_6R_7$ groups in which $R_6$ and $R_7$ are, independently of one another, chosen from H and linear and branched $C_1$–$C_4$ alkyl radicals; it being possible for $R_6$ and $R_7$, taken together, to form a 5- or a 6-membered ring, and —O(CO)$R_8$ groups in which $R_8$ is chosen from H and linear and branched $C_1$–$C_8$ alkyl radicals;

Z is chosen from compounds of formula (II) and formula (III)

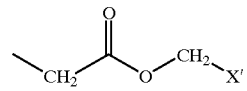

(II)

-continued

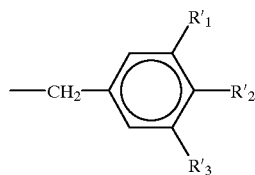

(III)

in which:
R'₁, R'₂ and R'₃ are, independently of one another, chosen from H, OH, and linear and branched $C_1$–$C_8$ alkoxy radicals;
X' is chosen from —(CO)NR'₄R'₅ groups in which R'₄ and R'₅ are, independently of one another, chosen from H and linear and branched $C_1$–$C_4$ alkyl radicals; it being possible for R'₄ and R'₅, taken together, to form a 5- or a 6-membered ring, and —O(CO)R'₆ groups in which R'₆ is chosen from H and linear and branched $C_1$–$C_8$ alkyl radicals.

2. The compound according to claim 1, wherein the alkoxy radicals are independently of one another, chosen from methoxy, ethoxy, n-propyloxy, isopropyloxy, n-butyloxy, sec-butyloxy and tert-butyloxy radicals and wherein the alkyl radicals are, independently of one another, chosen from methyl, ethyl, n-propyl, isopropyl, n-butyl, sec-butyl and tert-butyl radicals.

3. The compound according to claim 1, wherein said inorganic or organic salt is chosen from sulphates, hydrochlorides, nitrates, phosphates, bromates, fumarates, mesylates and tosylates.

4. The compound according to claim 1, wherein said compound is chosen from
 bis(acetoxymethyl) [N,N'-bis(3,4,5trimethoxybenzyl)] ethylenediamine-N,N'-diacetate,
 bis(pivaloyloxymethyl) [N,N'-bis(3,4,5trimethoxybenzyl)]ethylenediamine-N,N'-diacetate,
 bis(N,N-diethylaminocarbonylmethyl) [N,N'-bis(3,4,5-trimethoxybenzyl)]ethylenediamine-N,N'-diacetate,
and salts thereof.

5. The compound according to claim 1, wherein said salts are hydrochlorides.

6. A cosmetic or pharmaceutical composition, comprising, in a cosmetically or pharmaceutically acceptable vehicle, at least one ingredient chosen from compounds of formula (I) and salts thereof:

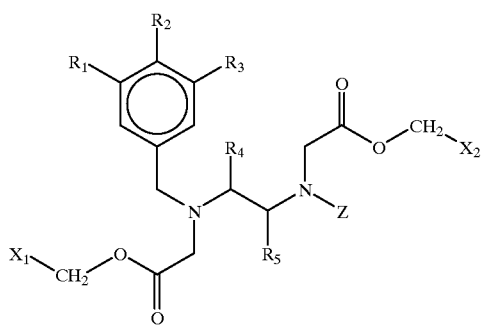

wherein:
R₁, R₂ and R₃ are, independently of one another, chosen from H, OH and linear and branched $C_1$–$C_8$ alkoxy radicals;

R₄ and R₅ are, independently of one another, chosen from H and linear and branched $C_1$–$C_4$ alkyl radicals; it being possible for R₄ and R₅, taken together, to form a 5- or a 6-membered ring;
X₁ and X₂ are, independently of one another, chosen from —(CO)NR₆R₇ groups in which R₆ and R₇ are, independently of one another, chosen from H and linear and branched $C_1$–$C_4$ alkyl radicals; it being possible for R₆ and R₇, taken together, to form a 5- or a 6-membered ring, and
—O(CO)R₈ groups in which R₈ is chosen from H and linear and branched $C_1$–$C_8$ alkyl radicals;
Z is chosen from compounds of formula (II) and formula (III)

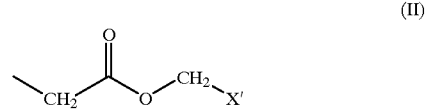

(II)

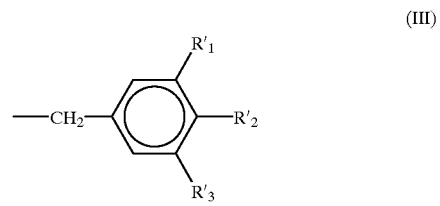

(III)

in which:
R'₁, R'₂ and R'₃ are, independently of one another, chosen from H, OH, and linear and branched $C_1$–$C_8$ alkoxy radicals;
X' is chosen from —(CO)NR'₄R'₅ groups in which R₄ and R'₅ are, independently of one another, chosen from H and linear and branched $C_1$–$C_4$ alkyl radicals; it being possible for R'₄ and R'₅, taken together, to form a 5- or a 6-membered ring, and —O(CO)R'₆ groups in which R'₆ is chosen from H and linear and branched $C_1$–$C_8$ alkyl radicals.

7. The composition according to claim 6, wherein said at least one ingredient is present in an amount of 0.001 to 10% by weight with respect to the total weight of the composition.

8. The composition according to claim 7, wherein said at least one ingredient is present in an amount of 0.01 to 8% by weight with respect to the total weight of the composition.

9. The composition according to claim 8, wherein said at least one ingredient is present in an amount of 0.1 to 5% by weight with respect to the total weight of the composition.

10. The composition according to claim 6, further comprising at least one other active substance.

11. The composition according to claim 10, wherein said at least one other active substance is chosen from substances for combating free radicals.

12. The composition according to claim 10, wherein said at least one other active substance chosen from antilipoperoxidizing agents, biological reducing agents, singlet oxygen deactivators, systems capable of decomposing hydrogen peroxide, systems for protecting against a superoxide anion, systems capable of decomposing an organic hydroperoxide, iron-chelating agents, anti-inflammatories, UV screening agents and penetration promoters.

13. The composition according to claim 6, wherein said composition is in the form of a salve, cream, ointment, gel, spray, lotion, emulsion or vesicular dispersion.

14. An antioxidizing agent comprising at least one ingredient chosen from compounds of formula (I) and salts thereof:

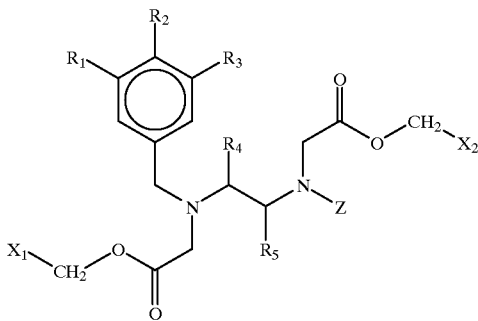

werein:

R₁, R₂ and R₃ are, independently of one another, chosen from H, OH and linear and branched $C_1$–$C_8$ alkoxy radicals;

R₄ and R₅ are, independently of one another, chosen from H and linear and branched $C_1$–$C_4$ alkyl radicals; it being possible for R₄ and R₅, taken together, to form a 5- or a 6-membered ring;

X₁ and X₂ are, independently of one another, chosen from —(CO)NR₆R₇ groups in which R₆ and R₇ are, independently of one another, chosen from H and linear and branched $C_1$–$C_4$ alkyl radicals; it being possible for R₆ and R₇, taken together, to form a 5- or a 6-membered ring, and
—O(CO)R₈ groups in which R₈ is chosen from H and linear and branched $C_1$–$C_8$ alkyl radicals;

Z is chosen from compounds of formula (II) and formula (III)

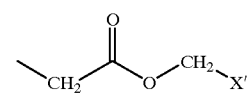
(II)

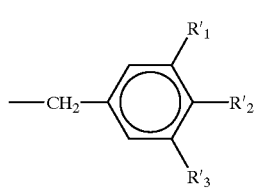
(III)

in which:

R'₁, R'₂ and R'₃ are, independently of one another, chosen from H, OH, and linear and branched $C_1$–$C_8$ alkoxy radicals;

X' is chosen from —(CO)NR'₄R'₅ groups in which R'₄ and R'₅ are, independently of one another, chosen from H and linear and branched $C_1$–$C_4$ alkyl radicals; it being possible for R'₄ and R'₅, taken together, to form a 5- or a 6-membered ring, and —O(CO)R'₆ groups in which R'₆ is chosen from H and linear and branched $C_1$–$C_8$ alkyl radicals.

15. A method of treating oxidative stress comprising applying to the body a cosmetic composition, wherein the cosmetic composition comprises at least one ingredient chosen from compounds of formula (I) and salts thereof:

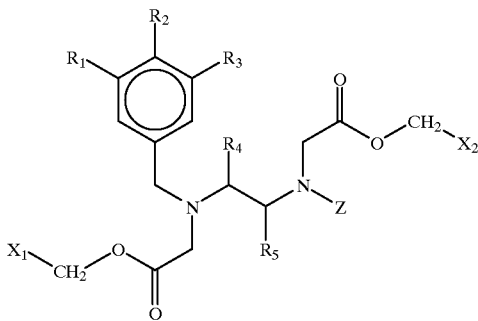

wherein:

R₁, R₂ and R₃ are, independently of one another, chosen from H, OH and linear and branched $C_1$–$C_8$ alkoxy radicals;

R₄ and R₅ are, independently of one another, chosen from H and linear and branched $C_1$–$C_4$ alkyl radicals; it being possible for R₄ and R₅, taken together, to form a 5- or a 6-membered ring;

X₁ and X₂ are, independently of one another, chosen from —(CO)NR₆R₇ groups in which R₆ and R₇ are, independently of one another, chosen from H and linear and branched $C_1$–$C_4$ alkyl radicals; it being possible for R₆ and R₇, taken together, to form a 5- or a 6-membered ring, and
—O(CO)R₈ groups in which R₈ is chosen from H and linear and branched $C_1$–$C_8$ alkyl radicals;

Z is chosen from compounds of formula (II) and formula (III)

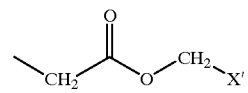
(II)

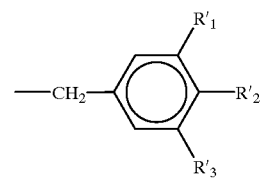
(III)

in which:

R'₁, R'₂ and R'₃ are, independently of one another, chosen from H, OH, and linear and branched $C_1$–$C_8$ alkoxy radicals;

X' is chosen from —(CO)NR'₄R'₅ groups in which R'₄ and R'₅ are, independently of one another, chosen from H and linear and branched $C_1$–$C_4$ alkyl radicals; it being possible for R'₄ and R'₅, taken together, to form a 5- or a 6-membered ring, and —O(CO)R'₆ groups in which R'₆ is chosen from H and linear and branched $C_1$–$C_8$ alkyl radicals.

16. The method of claim 15, comprising applying said cosmetic composition to the hair or skin.

17. A method of treating the effects of exposure to the sun comprising applying to the body a cosmetic composition, wherein the cosmetic composition comprises at least one ingredient chosen from compounds of formula (I) and salts thereof:

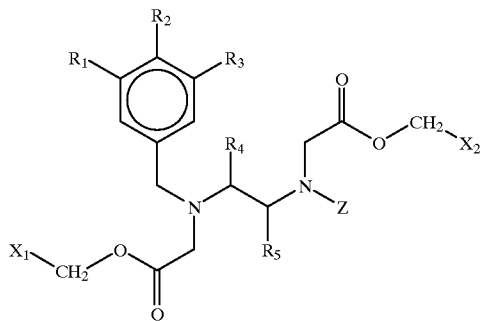

wherein:

R₁, R₂ and R₃ are, independently of one another, chosen from H, OH and linear and branched $C_1$–$C_8$ alkoxy radicals;

R₄ and R₅ are, independently of one another, chosen from H and linear and branched $C_1$–$C_4$ alkyl radicals; it being possible for R₄ and R₅, taken together, to form a 5- or a 6-membered ring;

X₁ and X₂ are, independently of one another, chosen from —(CO)NR₆R₇ groups in which R₆ and R₇ are, independently of one another, chosen from H and linear and branched $C_1$–$C_4$ alkyl radicals; it being possible for R₆ and R₇, taken together, to form a 5- or a 6-membered ring, and —O(CO)R₈ groups in which R₈ is chosen from H and linear and branched $C_1$–$C_8$ alkyl radicals;

Z is chosen from compounds of formula (II) and formula (III)

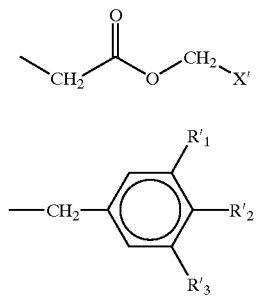

in which:

R'₁, R'₂ and R'₃ are, independently of one another, chosen from H, OH, and linear and branched $C_1$–$C_8$ alkoxy radicals;

X' is chosen from —(CO)NR'₄R'₅ groups in which R'₄ and R'₅ are, independently of one another, chosen from H and linear and branched $C_1$–$C_4$ alkyl radicals; it being possible for R'₄ and R'₅, taken together, to form a 5- or a 6membered ring, and —O(CO)R'₆ groups in which R'₆ is chosen from H and linear and branched $C_1$–$C_8$ alkyl radicals.

18. The method of claim 17, comprising applying said cosmetic composition to the skin or hair.

19. A cosmetic or pharmaceutical composition for treating oxidative stress, wherein the composition comprises at least one ingredient chosen from compounds of formula (I) and salts thereof:

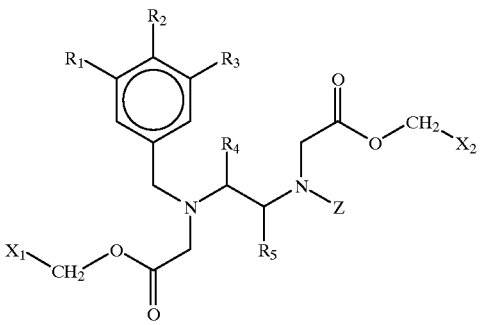

wherein:

R₁, R₂ and R₃ are, independently of one another, chosen from H, OH and linear and branched $C_1$–$C_8$ alkoxy radicals;

R₄ and R₅ are, independently of one another, chosen from H and linear and branched $C_1$–$C_4$ alkyl radicals; it being possible for R₄ and R₅, taken together, to form a 5- or a 6-membered ring;

X₁ and X₂ are, independently of one another, chosen from —(CO)NR₆R₇ groups in which R₆ and R₇ are, independently of one another, chosen from H and linear and branched $C_1$–$C_4$ alkyl radicals; it being possible for R₆ and R₇, taken together, to form a 5- or a 6-membered ring, and —O(CO)R₈ groups in which R₈ is chosen from H and linear and branched $C_1$–$C_8$ alkyl radicals;

Z is chosen from compounds of formula (II) and formula (III)

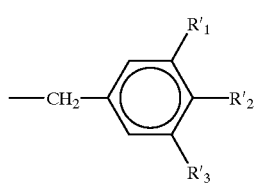

in which:

R'₁, R'₂ and R'₃ are, independently of one another, chosen from H, OH, and linear and branched $C_1$–$C_8$ alkoxy radicals;

X' is chosen from —(CO)NR'₄R'₅ groups in which R'₄ and R'₅ are, independently of one another, chosen from H and linear and branched $C_1$–$C_4$ alkyl radicals; it being possible for R'₄ and R'₅, taken together, to form a 5- or a 6-membered ring, and —O(CO)R'₆ groups in which R'₆ is chosen from H and linear and branched $C_1$–$C_8$ alkyl radicals.

20. A cosmetic composition for treating the effects of exposure to the sun, wherein the cosmetic composition comprises at least one ingredient chosen from compounds of formula (I) and salts thereof:

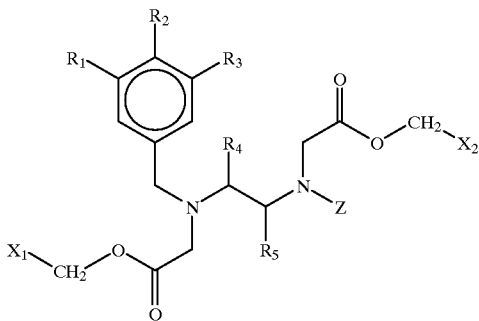

wherein:

- $R_1$, $R_2$ and $R_3$ are, independently of one another, chosen from H, OH and linear and branched $C_1$–$C_8$ alkoxy radicals;
- $R_4$ and $R_5$ are, independently of one another, chosen from H and linear and branched $C_1$–$C_4$ alkyl radicals; it being possible for $R_4$ and $R_5$, taken together, to form a 5- or a 6-membered ring;
- $X_1$ and $X_2$ are, independently of one another, chosen from —(CO)$NR_6R_7$ groups in which $R_6$ and $R_7$ are, independently of one another, chosen from H and linear and branched $C_1$–$C_4$ alkyl radicals; it being possible for $R_6$ and $R_7$, taken together, to form a 5- or a 6-membered ring, and —O(CO)$R_8$ groups in which $R_8$ is chosen from H and linear and branched $C_1$–$C_8$ alkyl radicals;
- Z is chosen from compounds of formula (II) and formula (III)

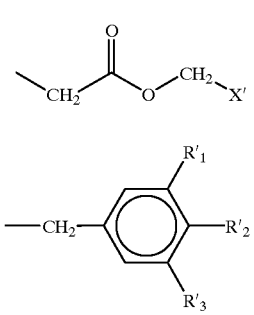

(II)

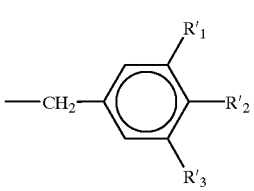

(III)

in which:

- $R'_1$, $R'_2$ and $R'_3$ are, independently of one another, chosen from H, OH, and linear and branched $C_1$–$C_8$ alkoxy radicals;
- X' is chosen from —(CO)$NR'_4R'_5$ groups in which $R'_4$ and $R'_5$ are, independently of one another, chosen from H and linear and branched $C_1$–$C_4$ alkyl radicals; it being possible for $R'_4$ and $R'_5$, taken together, to form a 5- or a 6-membered ring, and —O(CO)$R'_6$ groups in which $R'_6$ is chosen from H and linear and branched $C_1$–$C_8$ alkyl radicals.

21. A method of treating oxidative stress, comprising administering to a subject in need thereof a pharmaceutical composition, wherein the pharmaceutical composition comprises at least one ingredient chosen from compounds of formula (I) and salts thereof:

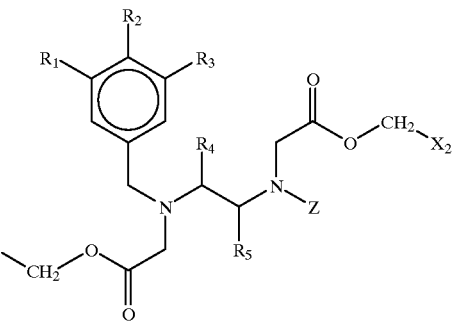

wherein:

- $R_1$, $R_2$ and $R_3$ are, independently of one another, chosen from H, OH and linear and branched $C_1$–$C_8$ alkoxy radicals;
- $R_4$ and $R_5$ are, independently of one another, chosen from H and linear and branched $C_1$–$C_4$ alkyl radicals; it being possible for $R_4$ and $R_5$, taken together, to form a 5- or a 6-membered ring;
- $X_1$ and $X_2$ are, independently of one another, chosen from —(CO)$NR_6R_7$ groups in which $R_6$ and $R_7$ are, independently of one another, chosen from H and linear and branched $C_1$–$C_4$ alkyl radicals; it being possible for $R_6$ and $R_7$, taken together, to form a 5- or a 6-membered ring, and —O(CO)$R_8$ groups in which $R_8$ is chosen from H and linear and branched $C_1$–$C_8$ alkyl radicals;
- Z is chosen from compounds of formula (II) and formula (III)

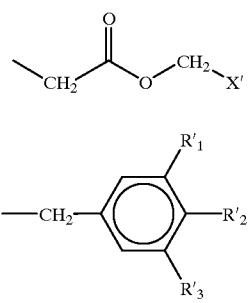

(II)

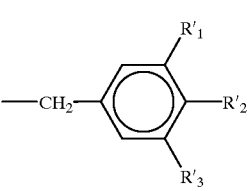

(III)

in which:

- $R'_1$, $R'_2$ and $R'_3$ are, independently of one another, chosen from H, OH, and linear and branched $C_1$–$C_8$ alkoxy radicals;
- X' is chosen from —(CO)$NR'_4R'_5$ groups in which $R'_4$ and $R'_5$ are, independently of one another, chosen from H and linear and branched $C_1$–$C_4$ alkyl radicals; it being possible for $R'_4$ and $R'_5$, taken together, to form a 5- or a 6-membered ring, and —O(CO)$R'_6$ groups in which $R'_6$ is chosen from H and linear and branched $C_1$–$C_8$ alkyl radicals.

22. A method of treating the effects of exposure to radiation, comprising administering to a subject in need thereof a pharmaceutical composition, wherein the pharmaceutical composition comprises at least one ingredient chosen from compounds of formula (I) and salts thereof:

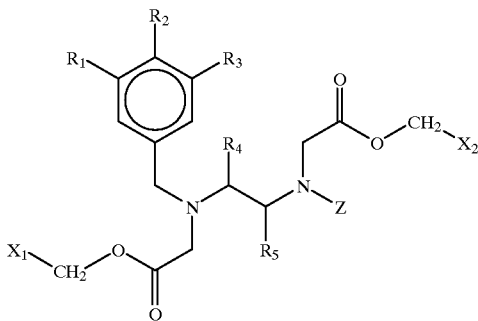

(I)

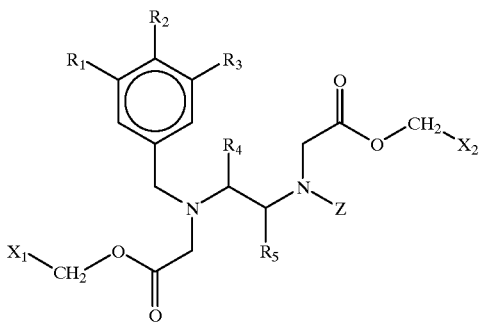

wherein:

$R_1$, $R_2$ and $R_3$ are, independently of one another, chosen from H, OH and linear and branched $C_1$–$C_8$ alkoxy radicals;

$R_4$ and $R_5$ are, independently of one another, chosen from H and linear and branched $C_1$–$C_4$ alkyl radicals; it being possible for $R_4$ and $R_5$, taken together, to form a 5- or a 6-membered ring;

$X_1$ and $X_2$ are, independently of one another, chosen from —(CO)$NR_6R_7$ groups in which $R_6$ and $R_7$ are, independently of one another, chosen from H and linear and branched $C_1$–$C_4$ alkyl radicals; it being possible for $R_6$ and $R_7$, taken together, to form a 5- or a 6-membered ring, and —O(CO)$R_8$ groups in which $R_8$ is chosen from H and linear and branched $C_1$–$C_8$ alkyl radicals;

Z is chosen from compounds of formula (II) and formula (III)

(II)

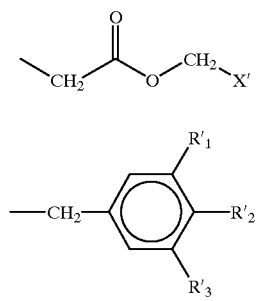

(III)

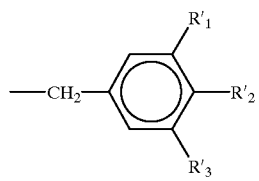

in which:

$R'_1$, $R'_2$ and $R'_3$ are, independently of one another, chosen from H, OH, and linear and branched $C_1$–$C_8$ alkoxy radicals;

X' is chosen from —(CO)$NR'_4R'_5$ groups in which $R'_4$ and $R'_5$ are, independently of one another, chosen from H and linear and branched $C_1$–$C_4$ alkyl radicals; it being possible for $R'_4$ and $R'_5$, taken together, to form a 5- or a 6-membered ring, and —O(CO)$R'_6$ groups in which $R'_6$ is chosen from H and linear and branched $C_1$–$C_8$ alkyl radicals.

23. The method of claim 22, wherein the radiation is solar or ionizing.

24. A pharmaceutical composition for treating an effect of exposure to ionizing or solar radiation, wherein the pharmaceutical composition comprises at least one ingredient chosen from compounds of formula (I) and salts thereof:

wherein:

$R_1$, $R_2$ and $R_3$ are, independently of one another, chosen from H, OH and linear and branched $C_1$–$C_8$ alkoxy radicals;

$R_4$ and $R_5$ are, independently of one another, chosen from H and linear and branched $C_1$–$C_4$ alkyl radicals; it being possible for $R_4$ and $R_5$, taken together, to form a 5- or a 6-membered ring;

$X_1$ and $X_2$ are, independently of one another, chosen from —(CO)$NR_6R_7$ groups in which $R_6$ and $R_7$ are, independently of one another, chosen from H and linear and branched $C_1$–$C_4$ alkyl radicals; it being possible for $R_6$ and $R_7$, taken together, to form a 5- or a 6-membered ring, and —O(CO)$R_8$ groups in which $R_8$ is chosen from H and linear and branched $C_1$–$C_8$ alkyl radicals;

Z is chosen from compounds of formula (II) and formula (III)

(II)

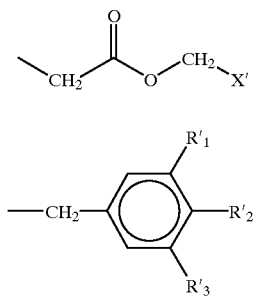

(III)

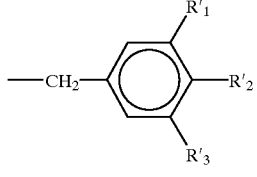

in which:

$R'_1$, $R'_2$ and $R'_3$ are, independently of one another, chosen from H, OH, and linear and branched $C_1$–$C_8$ alkoxy radicals;

X' is chosen from —(CO)$NR'_4R'_5$ groups in which $R'_4$ and $R'_5$ are, independently of one another, chosen from H and linear and branched $C_1$–$C_4$ alkyl radicals; it being possible for $R'_4$ and $R'_5$, taken together, to form a 5- or a 6-membered ring, and —O(CO)$R'_6$ groups in which $R'_6$ is chosen from H and linear and branched $C_1$–$C_8$ alkyl radicals; and wherein said at least one ingredient is present in an amount effective for treating an effect of exposure to ionizing or solar radiation.

25. A pharmaceutical composition for treating an effect of medicaments which generate free radicals, wherein the pharmaceutical composition comprises at least one ingredient chosen from compounds of formula (I) and salts thereof:

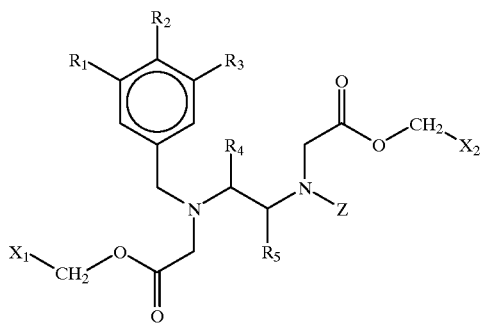 (I)

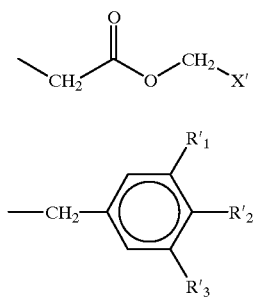

wherein:

$R_1$, $R_2$ and $R_3$ are, independently of one another, chosen from H, OH and linear and branched $C_1$–$C_8$ alkoxy radicals;

$R_4$ and $R_5$ are, independently of one another, chosen from H and linear and branched $C_1$–$C_4$ alkyl radicals; it being possible for $R_4$ and $R_5$, taken together, to form a 5- or a 6-membered ring;

$X_1$ and $X_2$ are, independently of one another, chosen from —(CO)$NR_6R_7$ groups in which $R_6$ and $R_7$ are, independently of one another, chosen from H and linear and branched $C_1$–$C_4$ alkyl radicals; it being possible for $R_6$ and $R_7$, taken together, to form a 5- or a 6-membered ring, and —O(CO)$R_8$ groups in which $R_8$ is chosen from H and linear and branched $C_1$–$C_8$ alkyl radicals;

Z is chosen from compounds of formula (II) and formula (III)

in which:

$R'_1$, $R'_2$ and $R'_3$ are, independently of one another, chosen from H, OH, and linear and branched $C_1$–$C_8$ alkoxy radicals;

X' is chosen from —(CO)$NR'_4R'_5$ groups in which $R'_4$ and $R'_5$ are, independently of one another, chosen from H and linear and branched $C_1$–$C_4$ alkyl radicals; it being possible for $R'_4$ and $R'_5$, taken together, to form a 5- or a 6-membered ring, and —O(CO)$R'_6$ groups in which $R'_6$ is chosen from H and linear and branched $C_1$–$C_8$ alkyl radicals; and wherein said at least one ingredient is present in an amount effective for treating an effect of medicaments which generate free radicals.

* * * * *

UNITED STATES PATENT AND TRADEMARK OFFICE
CERTIFICATE OF CORRECTION

PATENT NO.   : 6,218,432 B1
DATED        : April 17, 2001
INVENTOR(S)  : Jean-Baptiste Galey et al.

Page 1 of 1

It is certified that error appears in the above-identified patent and that said Letters Patent is hereby corrected as shown below:

Column 15, claim 17,
Line 59, "6membered" should read -- 6-membered --.

Signed and Sealed this

Eighth Day of January, 2002

Attest:

JAMES E. ROGAN
Attesting Officer    Director of the United States Patent and Trademark Office